United States Patent
Calisti et al.

(10) Patent No.: US 8,978,216 B2
(45) Date of Patent: Mar. 17, 2015

(54) METHOD FOR FORMING AN ACOUSTICAL STACK FOR AN ULTRASOUND PROBE

(75) Inventors: Serge Gerard Calisti, Bouches du Rhone (FR); Frederic Lanteri, Le Cannet (FR); Alan Tai, Phoenix, AZ (US); Charles Baumgartner, Niskayuna, NY (US); Jean-Francois Gelly, Mougins (FR)

(73) Assignee: General Electric Company, Schenectady, NY (US)

( * ) Notice: Subject to any disclaimer, the term of this patent is extended or adjusted under 35 U.S.C. 154(b) by 389 days.

(21) Appl. No.: 12/406,704

(22) Filed: Mar. 18, 2009

(65) Prior Publication Data

US 2010/0240998 A1    Sep. 23, 2010

(51) Int. Cl.
| | |
|---|---|
| H01L 41/22 | (2013.01) |
| H01L 41/37 | (2013.01) |
| H04R 31/00 | (2006.01) |
| A61B 8/00 | (2006.01) |
| G01S 7/52 | (2006.01) |
| H01L 41/18 | (2006.01) |

(Continued)

(52) U.S. Cl.
CPC . *A61B 8/00* (2013.01); *A61B 8/462* (2013.01); *A61B 8/565* (2013.01); *G01S 7/52084* (2013.01); *H01L 41/37* (2013.01); *H01L 41/183* (2013.01); *G06F 19/3406* (2013.01); *H01L 41/338* (2013.01)
USPC ............. 29/25.35; 29/594; 29/829; 29/852; 310/328; 310/334; 310/345

(58) Field of Classification Search
USPC ............. 29/25.35, 594, 841, 852, 23.35, 846, 29/829, 412, 417; 252/62.9 PZ; 310/324, 310/328
See application file for complete search history.

(56) References Cited

U.S. PATENT DOCUMENTS

| | | | | |
|---|---|---|---|---|
| 5,684,884 A | * | 11/1997 | Nakaya et al. ............ | 310/324 X |
| 5,894,646 A | * | 4/1999 | Hanafy et al. ............... | 29/25.35 |
| 5,998,910 A | * | 12/1999 | Park et al. .............. | 252/62.9 PZ |

(Continued)

FOREIGN PATENT DOCUMENTS

| | | | | | |
|---|---|---|---|---|---|
| JP | 56086598 A | * | 7/1981 | ............... | 29/25.35 X |
| JP | 63-164700 A | | 7/1988 | | |

(Continued)

OTHER PUBLICATIONS

Zhou et al., "Design and Fabrication of PZN-7%PT Single Crystal High Frequency Angled Needle Ultrasound Transducers", IEEE Transactions on Ultrasonics, Ferroelectrics, and Frequency Control; vol. 55, No. 6, Jun. 2008, pp. 1394-1399.*

(Continued)

*Primary Examiner* — A. Dexter Tugbang
(74) *Attorney, Agent, or Firm* — The Small Patent Law Group LLC; Dean Small (57) ABSTRACT

A method for forming an acoustical stack for an ultrasound probe comprises partly dicing a single crystal piezoelectric material to form single crystal pieces that are partly separated by a plurality of kerfs. The single crystal piezoelectric material comprises a carrier layer. The kerfs are filled with a kerf filling material to form a single crystal composite and the carrier layer is removed. At least one matching layer is attached to the single crystal composite, and dicing within the kerfs is accomplished to form separate acoustical stacks from the single crystal composite.

14 Claims, 11 Drawing Sheets

(51) Int. Cl.
*G06F 19/00* (2011.01)
*H01L 41/338* (2013.01)

(56) References Cited

U.S. PATENT DOCUMENTS

| | | | |
|---|---|---|---|
| 6,359,375 B1 * | 3/2002 | Guo et al. | 310/334 |
| 6,586,702 B2 | 7/2003 | Wiener-Avnear et al. | |
| 6,798,717 B2 | 9/2004 | Wiener-Avnear et al. | |
| 7,316,059 B2 * | 1/2008 | Sato | 29/25.35 X |

FOREIGN PATENT DOCUMENTS

| | | |
|---|---|---|
| JP | 04-006999 A | 1/1992 |
| JP | 07-131896 A | 5/1995 |
| JP | 07-231890 A | 9/1995 |
| JP | 09-238399 A | 9/1997 |
| JP | 10-117399 A | 5/1998 |
| JP | 2000-040676 A | 2/2000 |
| JP | 2004-097792 A | 4/2004 |
| JP | 2005-191828 A | 7/2005 |
| JP | 2007-036642 A | 2/2007 |
| WO | 2008-027673 A1 | 3/2008 |

OTHER PUBLICATIONS

Unofficial translation of JP Office Action from corresponding JP Patent Application No. 2010-060067 dated Feb. 4, 2014.

* cited by examiner

METHOD FOR FORMING AN ACOUSTICAL STACK FOR AN ULTRASOUND PROBE

BACKGROUND OF THE INVENTION

This invention relates generally to ultrasound probes, and more particularly, to acoustical stacks within the ultrasound probes.

Single crystal piezoelectric material may be used to form the acoustical stacks in ultrasound probes. The single crystal piezoelectric material is, however, a very fragile and brittle material that requires specific conditions for handling. For example, the material cannot sustain a high level of strain without losing some piezoelectric properties and easily develops material cracks that can propagate inside the material structure, resulting in localized changes in material properties.

Crack propagation as well as a high level of degradation may occur when the material is diced using a standard dicing saw without optimized conditions. Optimized conditions include fine-tuning of the dicing parameters, such as blade material, spindle speed of rotation, feeding speed, and the like. However, the manufacturing of an acoustical stack for use within an ultrasound probe requires that the piezoelectric material is stacked or sandwiched with other layers of materials such as graphite based materials or heavily loaded epoxy materials that may be used to form matching layers, flex materials with embedded copper traces, and/or other very hard material(s). To achieve acceptable throughput, the dicing parameters when dicing the stacked materials cannot be limited to the optimized conditions needed by the single crystal piezoelectric material because of the variety of materials and the total thickness. For example, optimized conditions require the feeding speed to be greatly reduced, resulting in increased manufacturing cost. Additionally, the blade material that is optimized to dice the single crystal piezoelectric material under optimized dicing parameters may not be appropriate for dicing the stacked materials.

BRIEF DESCRIPTION OF THE INVENTION

In one embodiment, a method for forming an acoustical stack for an ultrasound probe comprises partly dicing a single crystal piezoelectric material to form single crystal pieces that are partly separated by a plurality of kerfs. The single crystal piezoelectric material comprises a carrier layer. The kerfs are filled with a kerf filling material to form a single crystal composite and the carrier layer is removed. At least one matching layer is attached to the single crystal composite, and dicing within the kerfs is accomplished to form separate acoustical stacks from the single crystal composite.

In another embodiment, an ultrasound probe comprises an array of elements that include a plurality of single crystal pieces that are separated by a first set of kerfs. At least one matching layer is attached to one side of the single crystal pieces, and a flex circuit is attached to the other side of the single crystal pieces. The at least one matching layer and the flex circuit are separated into pieces by a second set of kerfs that are formed within the first set of kerfs, The flex circuit comprises traces that are configured to receive signals and ground from an ultrasound system.

In yet another embodiment, a method for forming an acoustical stack for an ultrasound probe comprises partly dicing a single crystal piezoelectric material in a first dicing operation that forms a first set of kerfs having a width. At least one matching layer is attached to one side of the single crystal piezoelectric material. A flex circuit is attached to an opposite side of the single crystal piezoelectric material, and dicing within the first set of kerfs is accomplished in a second dicing operation that has a width that is narrower than the width of the first set of kerfs to form separate acoustical stacks.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
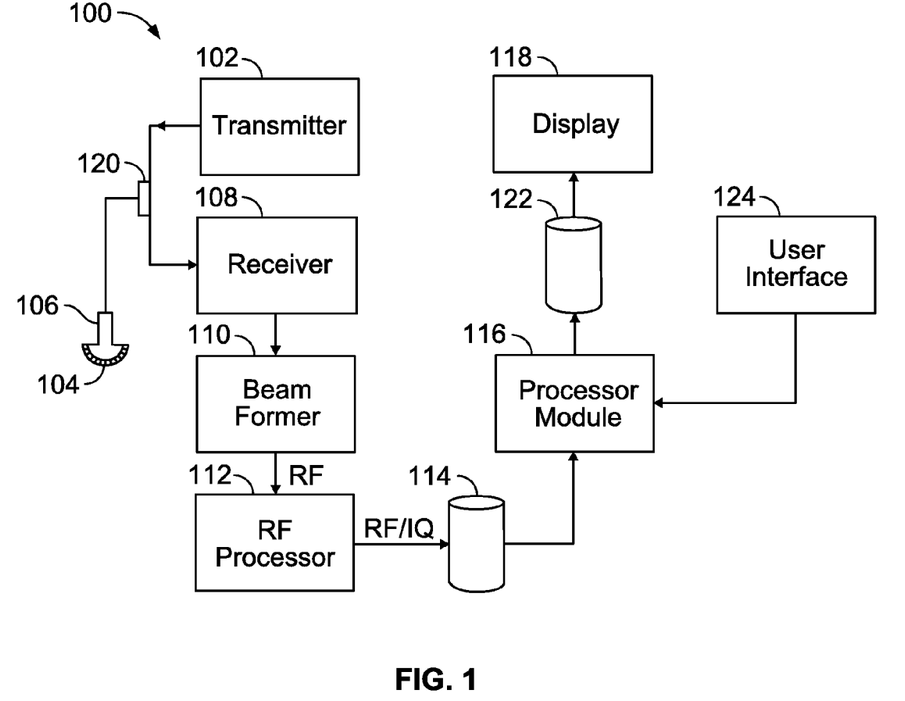
FIG. 1 illustrates an ultrasound system formed in accordance with an embodiment of the present invention.

FIG. 1 illustrates an ultrasound system 100 including a transmitter 102 that drives an array of elements 104 (e.g., piezoelectric elements) within a probe 106 to emit pulsed ultrasonic signals into a body. The elements 104 may comprise single crystal material and/or single crystal composite material as discussed herein. The elements 104 may be arranged, for example, in one or two dimensions. A variety of geometries may be used, and the probe 106 may be capable of acquiring one, two, three and/or four dimensional image data. The system 100 may have a probe port 120 for receiving the probe 106 or the probe 106 may be hardwired to the system 100.

The ultrasonic signals are back-scattered from structures in the body, like fatty tissue or muscular tissue, to produce echoes that return to the elements 104. The echoes are received by a receiver 108. The received echoes are passed through a beamformer 110 that performs beamforming and outputs a radiofrequency (RF) signal. The RF signal then passes through an RF processor 112. Alternatively, the RF processor 112 may include a complex demodulator (not shown) that demodulates the RF signal to form in-phase and quadrature (IQ) data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 or memory 122 during a scanning session and then processed and displayed in an off-line operation.

A user interface 124 may be used to input data to the system 100, adjust settings, and control the operation of the processor module 116. The user interface 124 may have a keyboard, trackball and/or mouse, and a number of knobs, switches or other input devices such as a touchscreen. The display 118 includes one or more monitors that present patient information, including diagnostic ultrasound images to the user for diagnosis and analysis. One or both of memory 114 and memory 122 may store two-dimensional (2D) and/or three-dimensional (3D) datasets of the ultrasound data, where such datasets are accessed to present 2D and/or 3D images. Multiple consecutive 3D datasets may also be acquired and stored over time, such as to provide real-time 3D or four-dimensional (4D) display. The images may be modified and the display settings of the display 118 also manually adjusted using the user interface 124.

Figure 2:
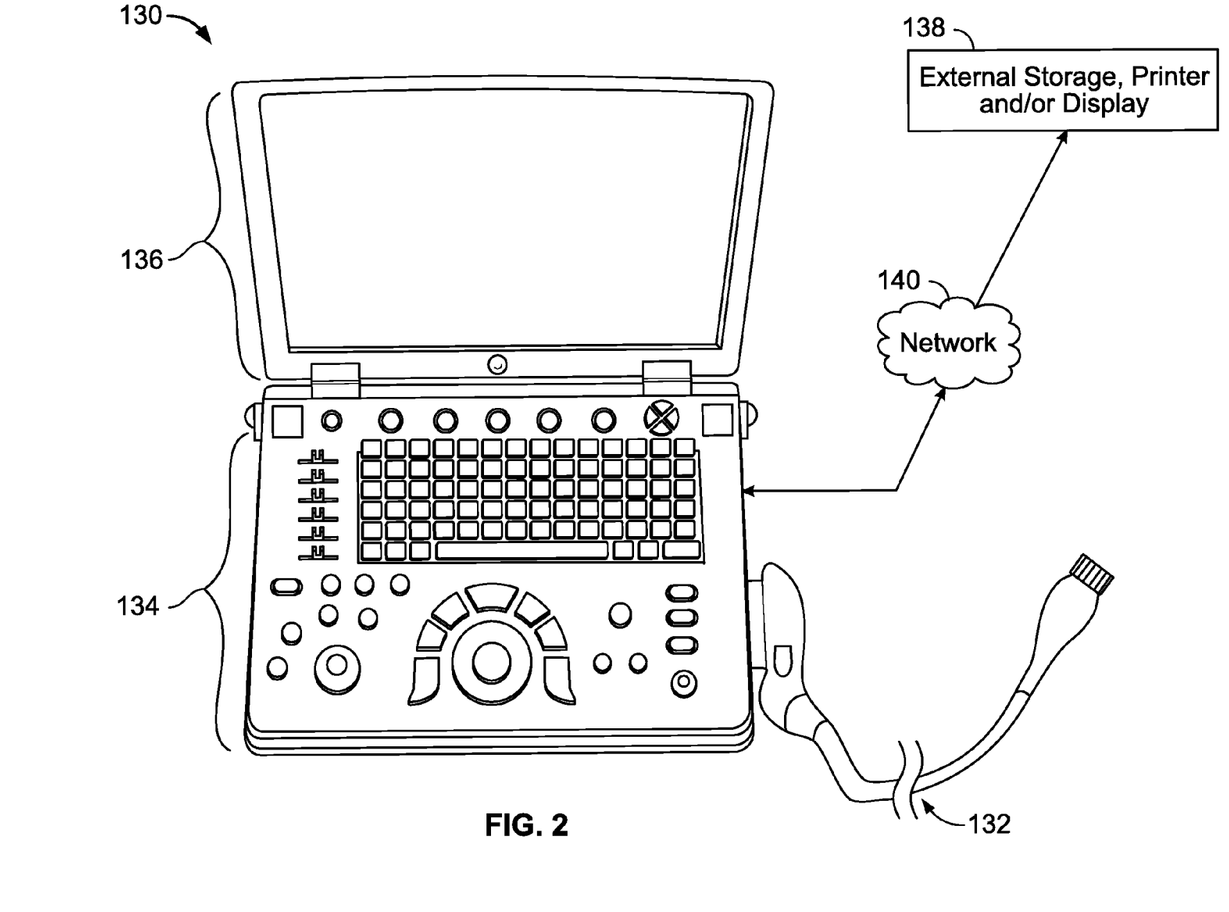
FIG. 2 illustrates a 3D-capable miniaturized ultrasound system that has a probe that may comprise single crystal and/or single crystal composite elements formed in accordance with an embodiment of the present invention.

FIG. 2 illustrates a 3D-capable miniaturized ultrasound system 130 having a probe 132 that may comprise elements 104 having single crystal material and/or single crystal composite material as discussed herein. The probe 132 may be configured to acquire 3D ultrasonic data. For example, the probe 132 may have a 2D array of transducer elements 104. A user interface 134 (that may also include an integrated display 136) is provided to receive commands from an operator.

As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136. It should be noted that the various embodiments may be implemented in connection with a miniaturized ultrasound system having different dimensions, weights, and power consumption.

Figure 3:
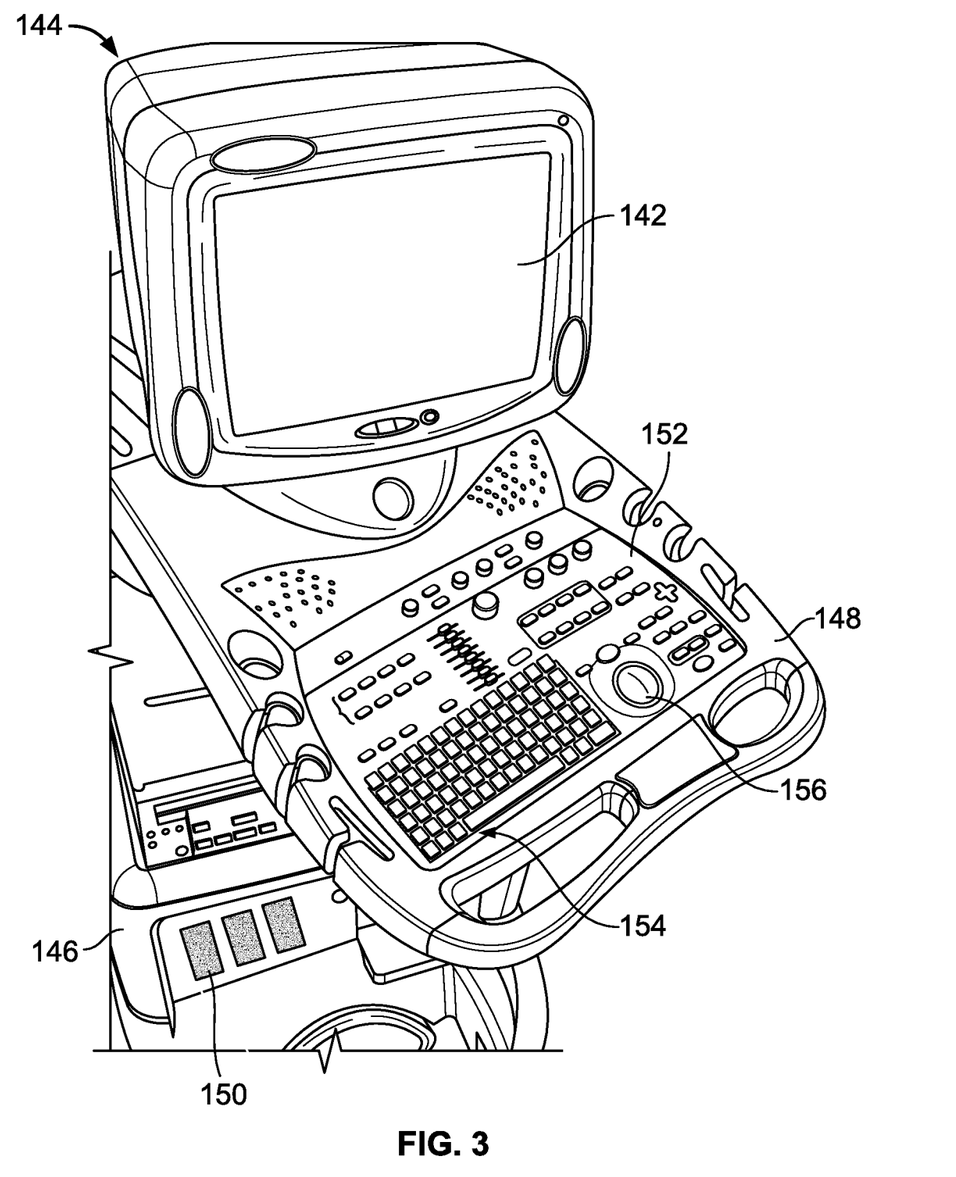
FIG. 3 illustrates a mobile ultrasound imaging system that may use a probe that may comprise single crystal and/or single crystal composite elements formed in accordance with an embodiment of the present invention.

FIG. 3 illustrates a mobile ultrasound imaging system 144 provided on a movable base 146. The ultrasound imaging system 144 may also be referred to as a cart-based system. A display 142 and user interface 148 are provided and it should be understood that the display 142 may be separate or separable from the user interface 148. The system 144 has at least one probe port 150 for accepting probes (not shown) that may have elements 104 that comprise single crystal material and/or or single crystal composite material as discussed herein.

The user interface 148 may optionally be a touchscreen, allowing the operator to select options by touching displayed graphics, icons, and the like. The user interface 148 also includes control buttons 152 that may be used to control the ultrasound imaging system 144 as desired or needed, and/or as typically provided. The user interface 148 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 154 and track ball 156 may be provided.

Figure 4:
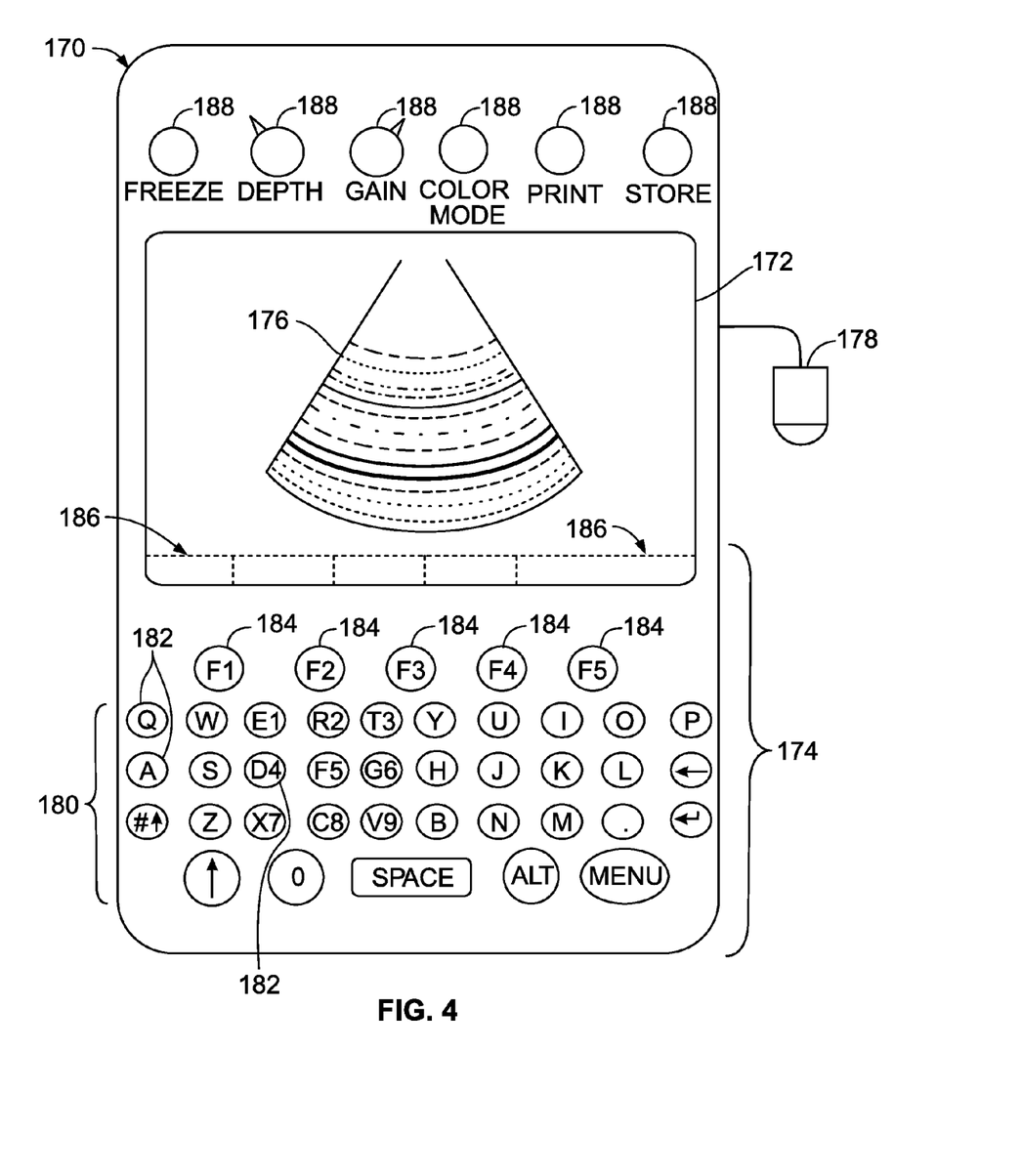
FIG. 4 illustrates a hand carried or pocket-sized ultrasound imaging system that has a probe that may comprise single crystal and/or single crystal composite elements formed in accordance with an embodiment of the present invention.

FIG. 4 illustrates a hand carried or pocket-sized ultrasound imaging system 170 wherein display 172 and user interface 174 form a single unit. By way of example, the pocket-sized ultrasound imaging system 170 may be approximately 2 inches wide, approximately 4 inches in length, and approximately 0.5 inches in depth and weighs less than 3 ounces. The display 172 may be, for example, a 320×320 pixel color LCD display (on which a medical image 176 may be displayed). A typewriter-like keyboard 180 of buttons 182 may optionally be included in the user interface 174. A probe 178 that has elements 104 comprising single crystal material and/or single crystal composite material as discussed herein is interconnected with the system 170.

Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 172. The system 170 may also have additional keys and/or controls 188 for special purpose functions, which may include, but are not limited to "freeze," "depth control," "gain control," "color-mode," "print," and "store."

The term acoustical stack may be used herein to refer to several layers that are attached together in a stacked configuration. Each of the elements 104 (shown in FIG. 1) within the probe 106 comprises an acoustical stack. In one embodiment, the acoustical stack includes a piezoelectric layer that is formed of a piezoelectric material such as single crystal piezoelectric material or a composite comprising single crystal piezoelectric material and at least one additional acoustically optimized material. The piezoelectric layer may have, for example, a thickness of approximately ½ or ¼ of Lamba $$\left(\frac{\lambda}{4}\right) \text{ or } \left(\frac{\lambda}{2}\right),$$

wherein λ is the wavelength of sound in the piezoelectric material for the desired center frequency of the useful bandwidth. Electrodes may be formed with a thin metallic layer and deposited on at least top and bottom sides of the piezoelectric material.

In general, one or more matching layers are attached to the top side of the piezoelectric layer to match the acoustic impedances between the piezoelectric layer and an exterior of the probe 106, which may be based on the acoustic impedance of a human or other subject to be scanned. In other embodiments, there may be two or three matching layers comprising different materials, or at least one matching layer may be formed of a graded impedance material. A dematching layer may be interconnected to the bottom side of the piezoelectric layer, and a backing block may be attached at a bottom side of the dematching layer or at the bottom side of the piezoelectric layer if the dematching layer is not used. Other stack configurations are contemplated.

As discussed previously, once the layers of material are assembled it is no longer possible to dice the acoustical stack using the optimized parameters (e.g. blade material, feeding speed, and the like) that are needed to dice the single crystal piezoelectric material (herein also referred to as single crystal and single crystal material). A technical effect of at least one embodiment is using more than one dicing operation to form the elements 104. Methods and apparatus are described wherein the a slab of single crystal is diced in a first dicing operation. The layers of material are then combined with the single crystal slab to form the acoustical stack, and a second dicing that does not contact the single crystal is accomplished to create the individual acoustical stacks that form the elements 104. It should be understood that more than two dicing operations may be used to create the individual elements 104. Different dicing parameters may be used in each of the dicing operations.

Figure 5:
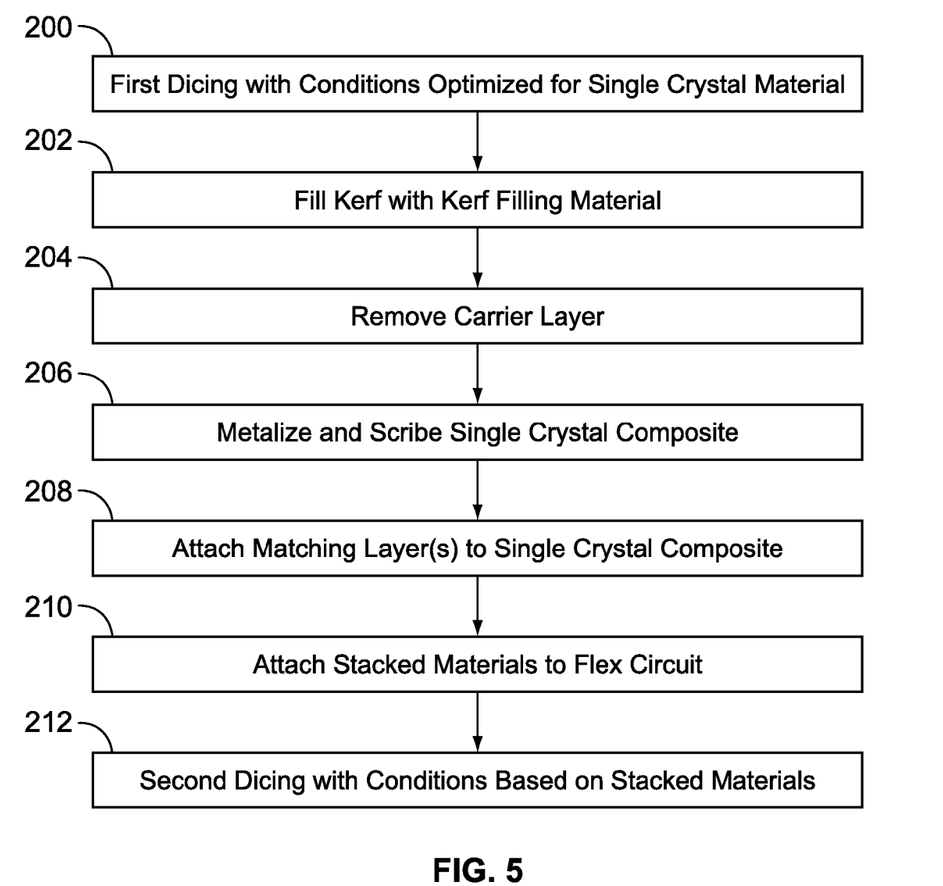
FIG. 5 illustrates a method for dicing the acoustical stack that includes single crystal within the piezoelectric layer in accordance with an embodiment of the present invention.

FIG. 5 illustrates a method for dicing the acoustical stack that includes single crystal piezoelectric material within the piezoelectric layer. At 200, a slab of single crystal piezoelectric material is partly diced in a first dicing operation using dicing parameters or conditions that are optimized for single crystal piezoelectric material. The terms partly diced and partial dicing as used herein refer to dicing material(s) partway through, such that the slab(s) of material(s) is maintained as a slab rather than individual pieces. The dicing parameters or conditions may be based on the mechanical properties and geometry of single crystal. Dicing parameters may include, but are not limited to, blade material, spindle speed of rotation, feeding speed and the like. Therefore, the quality of the single crystal is maintained while avoiding the cracking and degrading experienced when using dicing conditions that are needed when dicing an entire acoustical stack. In another embodiment, laser cutting, ion milling, chemical etching, wire dicing, plasma, and/or other processes or methods may be used, and may be optimized based on the single crystal material.

Figure 6:
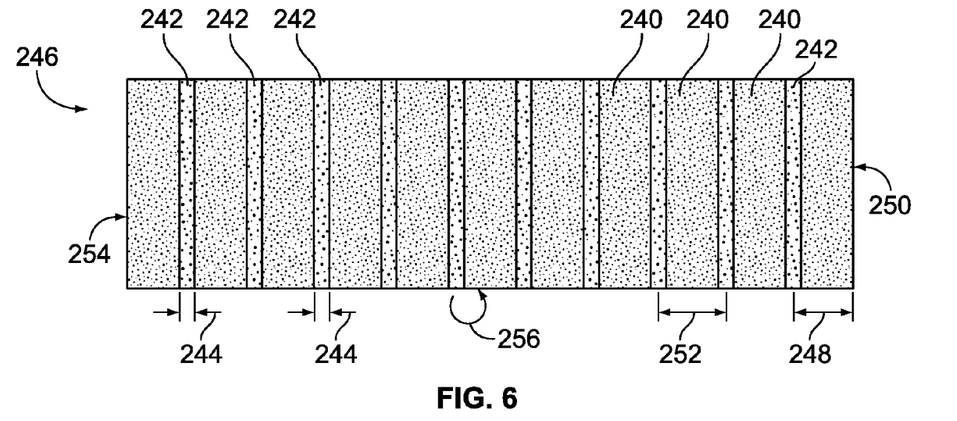
FIG. 6 illustrates a top view of single crystal piezoelectric material that is maintained on a carrier layer after being partly diced in accordance with an embodiment of the present invention.

The slab of single crystal material may be provided with a thickness larger than the acoustical-targeted thickness to include a layer of single crystal that may be referred to as a carrier layer. In one embodiment the slab of single crystal material may be a single piece of material, and in another embodiment the slab of single crystal material may be a stack of two or more slabs of single crystal material. The partial dicing at 200 does not extend through the carrier layer. FIG. 6 illustrates a top view of single crystal material after being partly diced. A carrier layer 256 extends along a bottom side of the single crystal material. A plurality of single crystal pieces 240 are shown and are maintained in relationship to one another by the carrier layer 256. Each of the single crystal pieces 240 corresponds to a single element 104 in the probe 106. A kerf 242 extending from the top side of the slab of single crystal material to the carrier layer 256 is formed between each of the single crystal pieces 240 by the cutting blade, or other cutting process or method as discussed previously, during the first dicing operation. Therefore, in one embodiment, the kerf 242 may be a trough, leaving a small amount of single crystal between the single crystal pieces 240. In another embodiment, the kerf 242 may be a separation, that is, the kerf 242 may completely separate the single crystal pieces 240. The kerf 242 has a width 244 corresponding to the width of the first dicing.

Returning to FIG. 5, at 202 the kerfs 242 are filled with a kerf filling material. The kerf filling material may be an organic polymer, epoxy based material, or other material that is suitable for both filling the kerf 242 and suitable for the subsequent dicing operation that will dice the acoustical stack. In general, the kerf filling material is substantially removed in a subsequent dicing operation and thus the mechanical properties of the kerf filling material may be considered while the acoustical properties of the kerf filling material are not important. As the single crystal is still held by the carrier layer 256, the single crystal pieces 240 and the kerf filling material in the kerfs 242 are fixed in place, thereby maintaining a desired relationship with respect to each other. The slab formed of the single crystal pieces 240 and kerfs 242 filled with kerf filling material may be referred to as single crystal composite 246. It should be noted that although the term composite is used, the elements 104 that will be formed from the single crystal composite 246 in this example comprise single crystal material that may have only a small amount of kerf filling material along one or two edges.

Referring to FIG. 6, the dimensions of the single crystal composite 246 are calibrated or predetermined. For example, a distance 248 from an outer edge 250 of the single crystal composite 246 to a center of a first kerf 242 is predetermined, as is a distance 252 from the center of one kerf 242 to the center of an adjacent kerf 242. In one embodiment, outer edges 250 and 254 of the single crystal composite 246 may be trimmed to predetermined dimensions to match alignment marks as discussed below.

Returning to FIG. 5, at 204 the carrier layer 256 may be removed. The single crystal pieces 240 are held in place by the kerf filling material, maintaining the single crystal composite 246 in a slab.

Figure 7:
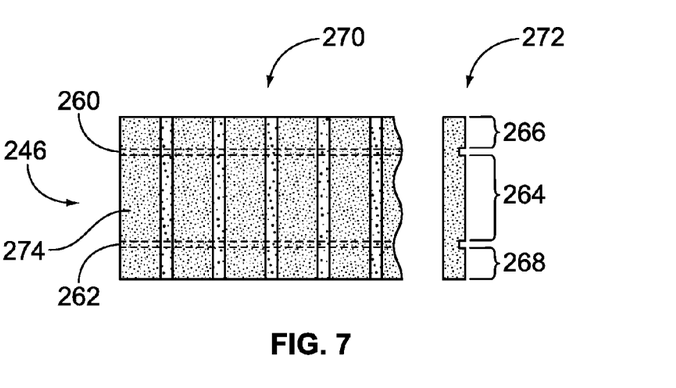
FIG. 7 illustrates several views of a single crystal composite after a conductive material has been applied in accordance with an embodiment of the present invention.

At 206 the single crystal composite 246 may be coated on all sides or surfaces, or at least the top and bottom sides, with a layer of a conductive material such as gold, nickel, a combination of conductive materials, and the like. FIG. 7 illustrates a top view 270 and an end view 272 of the single crystal composite 246 after conductive material 274 has been applied. Isolation scribings 260 and 262 may be made on one side of the single crystal composite 246 to define a signal area 264 and ground areas 266 and 268. It should be understood that other methods may be used to form electrodes and/or define signal and ground areas.

Figure 8:
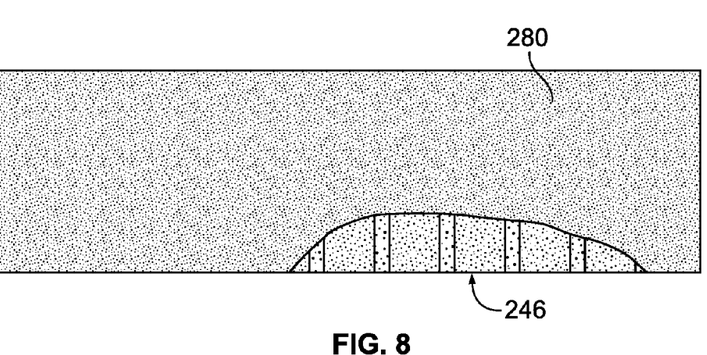
FIG. 8 illustrates a matching layer fixed to the single crystal composite in accordance with an embodiment of the present invention.

At 208 of the method of 200 of FIG. 5, at least one slab of material is attached to the single crystal composite 246. For example, at least one matching layer may be fixed, such as by using an adhesive, glue or other material, to the side of the single crystal composite 246 that does not have the isolation scribings 260 and 262. FIG. 8 illustrates an example of a matching layer 280 that has been fixed to the single crystal composite 246. A portion of the matching layer 280 has been removed to shown the single crystal composite 246. However, when forming the acoustical stack the matching layer 280 extends to be equal with all edges of the single crystal composite 246. Again, the stacked materials may be trimmed to desired dimensions.

Figure 9:
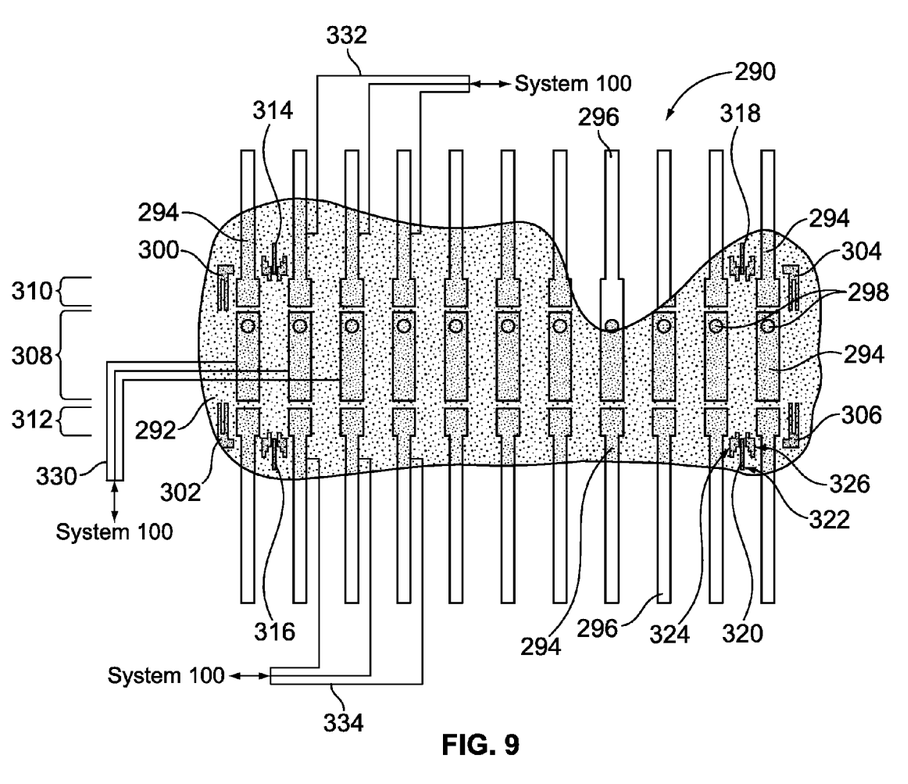
FIG. 9 illustrates a flex circuit formed in accordance with an embodiment of the present invention that is sandwiched or layered within the acoustical stack to interconnect the stack with the system of FIG. 1.

FIG. 9 illustrates an example of a flex circuit 290 that is sandwiched or layered within the acoustical stack to interconnect the stack with the system 100 (shown in FIG. 1). The flex circuit 290 has a flex insulation layer 292 that may be formed of a material such as Kapton, which is a polyimide film. Other materials may be used. Upper traces 294 are formed on one side of the flex insulation layer 292 and lower traces 296 are formed on the other side of the flex insulation layer 292. In one embodiment the upper and lower traces 294 and 296 may be copper or another metallic material or combination of materials, and may be printed on the flex insulation layer 292 using printing methods known in the art. The flex insulation layer 292 is partially removed to show a portion of the lower traces 296.

The upper traces 294 are formed in three separate areas, namely a central area 308 and outer areas 310 and 312. Although not shown, the lower traces 296 are formed in three corresponding separate areas. The portions of the upper and lower traces 294 and 296 within the central area 308 correspond to the signal area 264 of the single crystal composite 246 (as shown in FIG. 7) and the portions of the upper and lower traces 294 and 296 within outer areas 310 and 312 correspond to the ground areas 266 and 268. Signal lines 330 (not all are shown) configured to convey signals between the system 100 and the element 104 are connected through the lower traces 296 within the central area 308. Vias 298 are formed to extend through the flex insulation layer 292 and connect the upper and lower traces 294 and 296 to each other within the central area 308. Ground lines 332 and 334 (not all are shown) configured to provide ground potential from the system 100 are connected through the upper traces 294 within the outer areas 310 and 312. It should be understood that other configurations for conveying signal and ground may be used.

At least one edge alignment mark 300, 302, 304 and 306 is formed on the same side of the flex insulating layer 292 as the upper traces 294. The edge alignments mark(s) 300-306 are used to align the stacked materials, in this example the single crystal composite 246 and matching layer(s) 280, with respect to the flex circuit 290 as discussed below. In addition, at least one dicing alignment mark 314, 316, 318 and 320 is formed on the same side of the flex insulating layer 292 as the upper traces 294. The dicing alignment mark(s) 314-320 are used to identify the correct location to dice the stack so that the dicing operation cuts through the kerf filling material and does not touch the single crystal pieces 240. The alignment marks 300-306 and 314-320 may also be formed of a metallic material.

It should be understood that the shape and size of the edge alignment marks 300-306 and the dicing alignment marks 314-320 may vary and are not limited to the shapes, sizes and positions illustrated. As shown, the dicing alignment marks 314-320 each have a central portion 322 extending between two outer portions 324 and 326. The central portion 322 indicates the position for dicing, in other words, the dicing blade (or other dicing means, as applicable) is aligned to cut directly through the central portion 322. As shown, the edge alignment marks 300-306 are substantially "L" shaped. The stacked materials may be positioned such that each corner is positioned with respect to the "L" shape. In one embodiment, rather than being positioned relative to corners, the edge alignment marks 300-306 may be located at other positions with respect to the stacked materials, such as along one or more edge. In another embodiment, one or more of the dicing alignment marks 314-320 may be positioned to align with any of the kerfs 242.

Returning to FIG. 5, at 210 the stacked materials are attached to the flex circuit 290, such as by using glue or other adhesive, with the scribed side of the single crystal composite 246 facing the flex circuit 290. The stacked materials are positioned with respect to the flex circuit 290 by using the edge alignment mark(s) 300-306. For example, one or more corner, side or outer edge of the matching layer 280 may be aligned with the edge alignment mark 300-306. In one embodiment, a set of stud bumps or metal posts (not shown) may be formed on the top of the flex circuit 290 and the stacked materials may be aligned and fixed to the stud bumps using, for example, conductive glue. If needed, additional filler may be used between the flex circuit 290 and the stacked materials. In another embodiment, the matching layer(s) 280 may be fixed to the single crystal composite 246 after the single crystal composite 246 is attached to the flex circuit 290.

Figure 10:
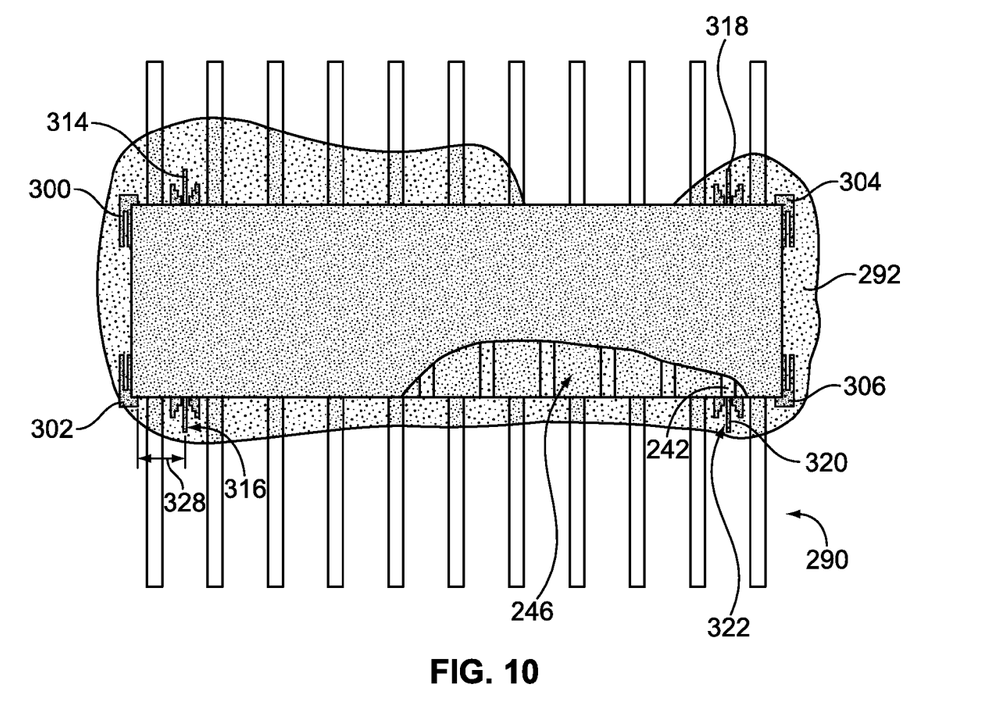
FIG. 10 illustrates the stacked materials that have been positioned and attached to the flex circuit of FIG. 9 in accordance with an embodiment of the present invention.

FIG. 10 illustrates the stacked materials that have been positioned and attached to the flex circuit 290. The edge alignment mark(s) 300-306 have been used to position the stacked materials. It can be seen that the central portion 322 of the dicing alignment mark 320 is positioned to extend through the center of the kerf 242.

In some embodiments no dicing alignment marks 314-320 may be provided and the positioning of the dicing blade, laser or other cutting means may be accomplished by measuring a predetermined distance from the edge alignment mark 300-306, such as distance 328 measured from the edge alignment mark 302. In some cases, glue or other adhesive that is used to fasten the stacked materials to the flex circuit 290 may extend beyond the slabs and obscure one or more of the edge alignment marks 300-306. Therefore, in other embodiments it may be desirable to provide at least one dicing alignment mark 314-320 to ensure correct positioning of the dicing blade. The dicing of the rest of the kerfs 242 may be measured with respect to the at least one dicing alignment mark 314-320 and/or at least one of the edge alignment marks 300-306.

Figure 11:
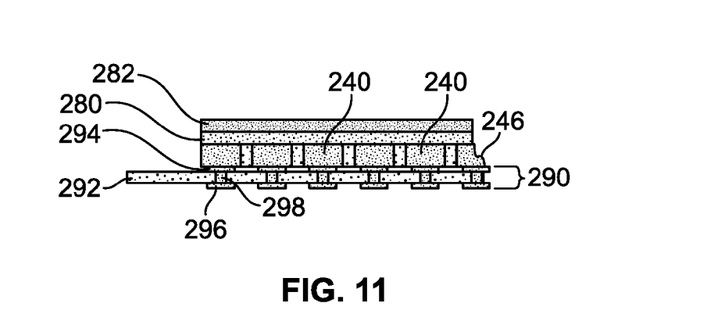
FIG. 11 illustrates a side view of the stacked materials attached to the flex circuit in accordance with an embodiment of the present invention.

FIG. 11 illustrates a side view of the stacked materials attached to the flex circuit 290. The vias 298 are shown extending through the flex insulating layer 292 to connect the upper and lower traces 294 and 296 to each other. The single crystal pieces 240 of the single crystal composite 246 are positioned on the flex circuit 290 over the upper traces 294. In one embodiment, the matching layer 280 is a first matching layer and second matching layer 282 is fixed to a top side of the matching layer 280.

Figure 12:
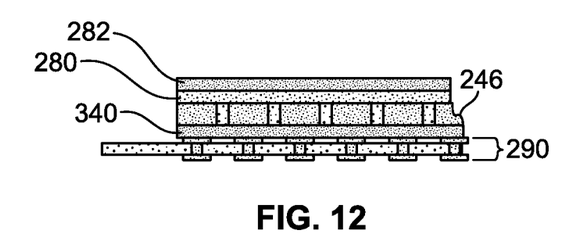
FIG. 12 illustrates an embodiment wherein a dematching layer is included in the stacked materials in accordance with an embodiment of the present invention.

FIG. 12 illustrates an alternative embodiment wherein a back side dematching layer 340 is included in the stacked materials. The dematching layer 340 may first be attached to the single crystal composite 246. The stacked materials may then be aligned with and attached to the flex circuit 290 as previously discussed. In another embodiment, the stacked materials may be attached after the single crystal composite 246 is attached to the flex circuit 290.

Figure 13:
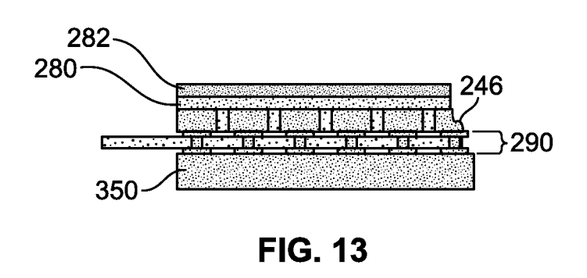
FIG. 13 illustrates an embodiment wherein a backing block is attached to the flex circuit in accordance with an embodiment of the present invention.

FIG. 13 illustrates an embodiment wherein a backing block 350 is attached to the side of the flex circuit 290 that has the lower traces 296. Although not shown, it should be understood that the backing block 350 may also be attached to the flex circuit 290 in the configuration of FIG. 12, wherein the dematching layer 340 is included in the stacked materials.

In some embodiments, other layers may be included in the stack, such as additional matching or dematching layers, electrodes in communication with the single crystal composite 246, and the like. Therefore, the methods and apparatus described herein are not limited to the illustrated stack configurations.

Returning to FIG. 5, at 212 the stacked materials, including at least the single crystal composite 246, at least one matching layer 280 and 282, and the flex circuit 290 are diced in a second dicing operation. The dicing parameters for the second dicing may be very different than for the first dicing due to the material differences that may include metal, graphite and other very hard materials, namely, materials that are harder than the single crystal material that was diced in the first dicing operation. Additionally, the stack thickness causes a larger exposure to the cutting blade. The dicing parameters, such as blade material and feeding speed, may be selected or optimized based on the slabs of material, such as the matching layer 280 and 282 and the flex insulating layer, 292 and do not have to take into account the single crystal material requirements. In other words, in this example the dicing parameters of the second dicing operation may be based on the mechanical properties of the matching layer 280 and 282 and the flex insulating layer 292.

Figure 14:
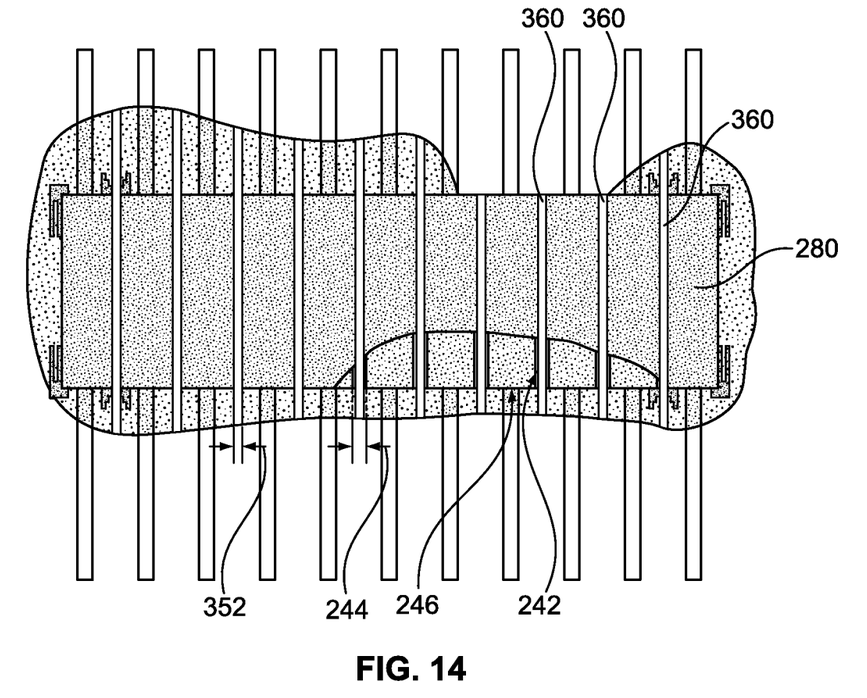
FIG. 14 illustrates a top view of the acoustical stack that has been diced in accordance with an embodiment of the present invention.

FIG. 14 illustrates a top view of the stack that has been diced. The dicing blade has diced the stacked materials into individual stacks by slicing through the kerf filling material within the kerfs 242. Part of the matching layer 280 is shown as a cut-away to show the single crystal composite 246. The second dicing has a width 352 that is less than the width 244 of the first dicing, and thus kerf 360 is thinner than the kerf 242. The kerfs 360 formed by the second dicing operation extend through the matching layer 280 and the kerf filling material of the single crystal composite 246. Therefore, the dicing blade dices into the kerf 242, removing some of the kerf filling material, but does not touch the single crystal pieces 240. In some embodiments, a small amount of kerf filling material remains on the edges of the single crystal pieces 240 and may protect the single crystal material during the second dicing.

In another embodiment, instead of accomplishing the second dicing operation using a dicing saw, a laser cutting technique may be used. In one embodiment, an ultraviolet (UV) laser may be used, although other types of lasers may also be used. In laser cutting, the moving of the parts and/or lasers may be controlled by a computer. The laser is directed and aimed on alignment marks, such as the dicing alignment marks 314-320, that are aligned with respect to the center of the kerf 242. The kerf filling material may be selected to absorb the energy of the laser, and thus the cutting operation may be performed in a relatively short time (such as less than one second) without overheating the single crystal pieces 240 on the edges of the kerf 242. In some embodiments, such as for thick layers or in special cases, a sweeping time and sweeping speed may be adjusted to realize ablation in multiple sweeps. In other words, the laser may quickly move from one end of the kerf 242 to the other end of the kerf 242 more than once so that the heat will not be localized in one spot.

Figure 15:
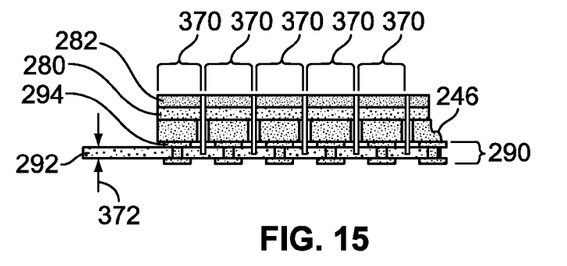
FIG. 15 illustrates the configuration of FIG. 11 that has been diced in accordance with an embodiment of the present invention.

FIG. 15 illustrates an example of the dicing operation based on the configuration of FIG. 11. The dicing saw (or laser) has sliced through the stacked materials and through a portion of a thickness 372 of the flex insulating layer 292, singularizing acoustical stacks 370 that correspond to the elements 104 (as shown in FIG. 1). A portion of the flex insulating layer 292 is maintained intact to hold the individual elements 104 (or acoustical stacks 370) with respect to each other.

Figure 16:
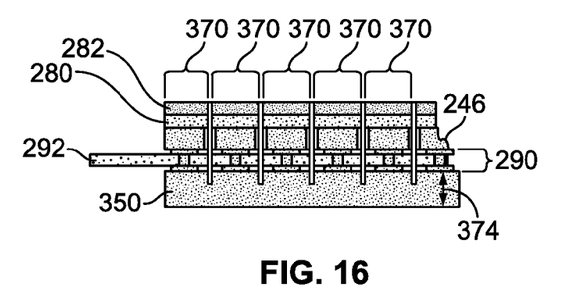
FIG. 16 illustrates the configuration of FIG. 13 that has been diced in accordance with an embodiment of the present invention.

In another embodiment shown in FIG. 16, an example of the dicing operation based on the configuration of FIG. 13 is illustrated. The dicing saw or laser has sliced through the stacked materials including the flex insulating layer 292, and through a portion of a thickness 374 of the backing block 350, forming the separate acoustical stacks 370. A portion of the backing block 350 is maintained intact to hold the individual elements 104 (or acoustical stacks 370) with respect to each other.

Although a single row of elements 104 is shown, it should be understood that multiple rows of elements 104 may be formed from larger slabs of stacked materials to form a 2D array of elements 104 that are held together with the flex insulating layer 292 (as shown in FIG. 15) or the backing block 350 (as shown in FIG. 16). In another embodiment, separate rows of elements 104 may be positioned with respect to each other and held together using other structures.

Figure 17:
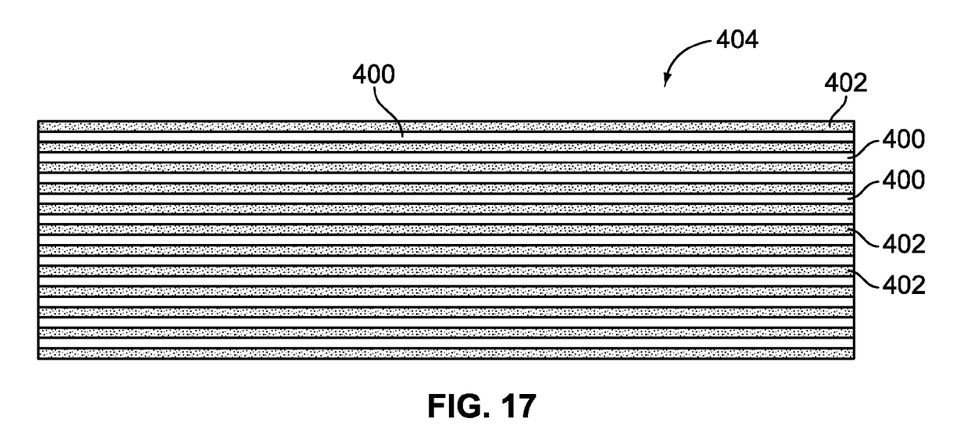
FIG. 17 illustrates an embodiment wherein a single crystal composite formed in accordance with an embodiment of the present invention comprises at least one additional acoustically optimized material.

FIG. 17 illustrates an embodiment wherein a single crystal composite 404 is formed that comprises at least one additional acoustically optimized material. Therefore, the acoustically optimized material is selected based on the acoustical properties of the material rather than the mechanical properties of the material. A slab of single crystal material may be diced to form single crystal strips 402 separated by a first set of kerfs 400. The first set of kerfs 400 may then be filled with a material that has been selected based on desired acoustical properties of the final composite material. Additionally, the ratio of kerf to single crystal material may be determined based on the desired acoustic properties of the single crystal composite 404. In one embodiment, the single crystal composite 404 may be approximately half single crystal material and half another acoustically optimized material. In another embodiment, at least one more acoustically optimized material may be used to fill some of the first set of kerfs 400. Although not shown, additional kerfs may be formed and/or one or more additional acoustically optimized material may be used, as may be encountered in piezo-composite slabs based on ceramics.

Figure 18:
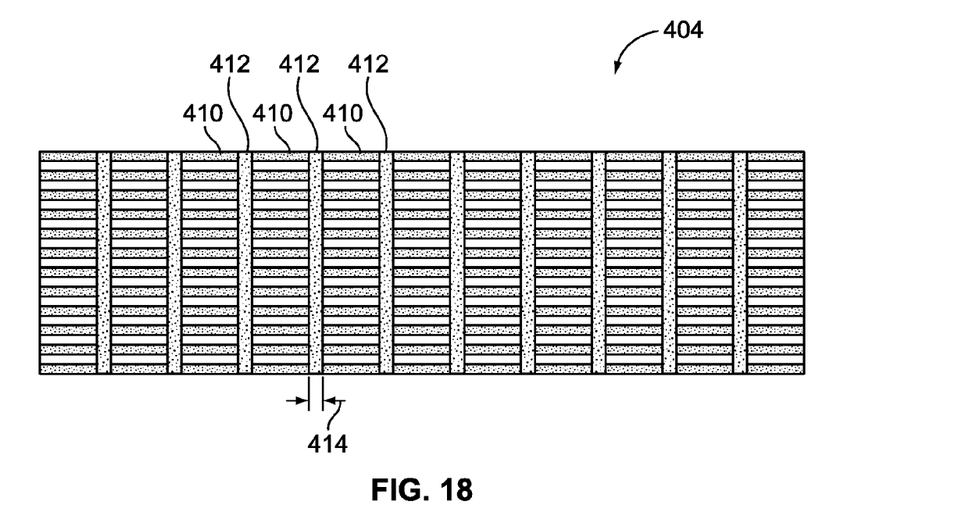
FIG. 18 illustrates dicing the single crystal composite of FIG. 17 to form composite pieces that are separated by a second set of kerfs in accordance with an embodiment of the present invention.

FIG. 18 illustrates dicing the single crystal composite 404 to form composite pieces 410 separated by a second set of kerfs 412. The dicing has a width 414. The second dicing direction may be, but is not limited to, perpendicular to the first dicing direction. The second set of kerfs 412 may be filled with the same kerf filling material as was used in FIG. 6, that is, a material that is mechanically optimized for dicing based on the stack parameters. The acoustic parameters of the material used to fill the second set of kerfs 412 are not necessarily important as the material will be substantially removed during a subsequent dicing operation. The thicknesses of materials used to fill the first and second sets of kerfs 400 and 412 may be adjusted at this point, if necessary.

Figure 19:
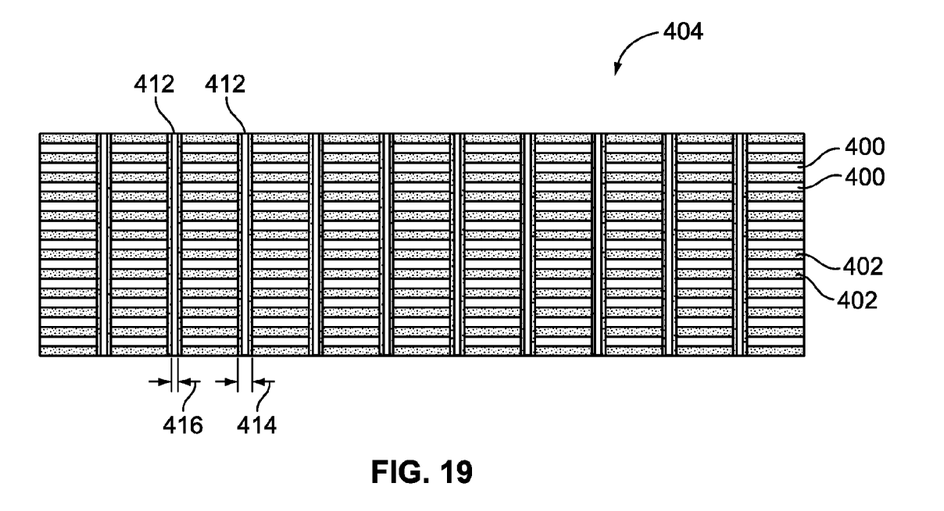
FIG. 19 illustrates the in-kerf dicing of the single crystal composite of FIG. 17 in accordance with an embodiment of the present invention.

FIG. 19 illustrates the in-kerf dicing of the single crystal composite 404. For simplicity, the other layers of the stack, such as the matching layer(s), flex circuit, alignment to the flex circuit, dematching layer, backing block and the like are not shown. FIG. 19 illustrates how the single crystal composite 404 may be diced within the second set of kerfs 412 without contacting the single crystal material. The in-kerf dicing has a width 416 that is less than the width 414. In this example, the material used to fill the first set of kerfs 400 is also not contacted by the dicing blade (or laser). Therefore, the dicing operation may be optimized based on the other layers of the stack without having to consider any special dicing parameters that may be based on the single crystal material or the material filling the first set of kerfs 400.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   dicing single crystal piezoelectric material to form single crystal pieces that are partly separated by plural kerfs, the single crystal piezoelectric material comprising a carrier layer along one side of a body of the single crystal piezoelectric material;
   filling the kerfs with a kerf filling material to form a single crystal composite;
   removing the carrier layer;
   attaching at least one matching layer to the single crystal composite;
   providing a flex circuit comprising at least one alignment mark disposed on a surface of the flex circuit;
   aligning the at least one matching layer with the at least one alignment mark on the surface of the flex circuit; and
   dicing within the kerfs at a predetermined distance from the at least one alignment mark to form separate acoustical stacks from the single crystal composite.

2. The method of claim 1, wherein the at least one alignment mark includes at least one edge alignment mark and aligning the at least one matching layer includes aligning at least one edge of the at least one matching layer with the at least one edge alignment mark, wherein dicing within the kerfs is performed at a predetermined distance from the at least one edge alignment mark.

3. The method of claim 1, wherein the flex circuit includes at least one dicing alignment mark, and further comprising aligning at least one of the kerfs with the at least one dicing alignment mark, wherein dicing within the kerfs is performed at one or more locations that are based on the at least one dicing alignment mark.

4. The method of claim 3, wherein the at least one dicing alignment mark is aligned with the at least one of the kerfs such that dicing the kerfs avoids dicing the single crystal pieces of the single crystal piezoelectric material.

5. The method of claim 1, wherein the kerf filling material is an organic material that is selected based on mechanical properties associated with dicing within the kerfs.

6. The method of claim 1, further comprising:
   partly dicing the single crystal piezoelectric material to form single crystal strips separated by an initial set of kerfs before forming the single crystal pieces; and,
   filling the initial set of kerfs with an acoustic material, the single crystal pieces comprising the single crystal piezoelectric material and the acoustic material.

7. The method of claim 1, wherein the kerfs comprise a first width formed by partly dicing the single crystal piezoelectric material, and wherein dicing within the kerfs forms troughs having a second width that is smaller than the width of the kerfs.

8. The method of claim 1, wherein dicing within the kerfs is accomplished with at least one of a blade, a laser, ion milling, or chemical etching.

9. The method of claim 1, wherein the flex circuit comprises a flex insulating layer, and wherein dicing within the kerfs includes dicing through a portion of a thickness of the flex insulating layer.

10. The method of claim 1, further comprising:
attaching the single crystal composite to a side of the flex circuit that includes a flex insulating layer having first conductive traces and second conductive traces formed on opposite sides of the flex insulating layer; and
attaching a backing block to the side of the flex circuit comprising the second conductive traces, wherein dicing within the kerfs includes dicing through a portion of a thickness of the backing block.

11. The method of claim 1, wherein dicing the single crystal piezoelectric material includes partly dicing the body of the single crystal piezoelectric material from an exposed side of the single crystal piezoelectric material toward the side to which the carrier layer is disposed.

12. The method of claim 11, wherein partly dicing the body of the single crystal piezoelectric material includes dicing the body from the exposed side toward the side of the body that is coupled with the carrier layer and through less than an entirety of a thickness of the body that extends from the exposed side to the side to which the carrier layer is coupled.

13. The method of claim 11, wherein the body of the single crystal piezoelectric material continuously extends from the exposed side to the side to which the carrier layer is coupled.

14. The method of claim 1, wherein the at least one alignment mark is spaced apart from edges of the flex circuit.

* * * * *